United States Patent [19]
Dixon

[11] Patent Number: 4,813,958
[45] Date of Patent: Mar. 21, 1989

[54] CROSSLINKED ANISOTROPIC MAMMALIAN DIAPHRAGM IN SURGICAL RECONSTRUCTION

[75] Inventor: France T. Dixon, Junipero, Calif.

[73] Assignee: Hancock Jaffe Laboratories, Irvine, Calif.

[21] Appl. No.: 918,032

[22] Filed: Oct. 14, 1986

[51] Int. Cl.$^4$ ............................................. A61F 2/02
[52] U.S. Cl. ...................................... 623/11; 623/13; 623/66; 128/DIG. 8; 128/897; 8/94.11; 8/94.19 R
[58] Field of Search ............... 8/94.1, 94.11, 94.19 R, 8/94.20; 128/1 R, DIG. 8; 623/1, 2, 11, 13, 66

[56] References Cited

U.S. PATENT DOCUMENTS

| | | | |
|---|---|---|---|
| 4,239,492 | 12/1980 | Holman et al. | 8/94.11 |
| 4,388,735 | 6/1983 | Ionescu et al. | 623/2 |
| 4,440,833 | 8/1983 | Karland | 623/13 |

Primary Examiner—Richard J. Apley
Assistant Examiner—Paul Prebilic
Attorney, Agent, or Firm—Grant L. Hubbard

[57] ABSTRACT

Anisotropic mammalian diaphragm is crosslinked using, for example, glutaraldehyde and used as a surgical implant graft for repair of tissues which accommodate to relative movement of tendons, joints, etc.

4 Claims, No Drawings

CROSSLINKED ANISOTROPIC MAMMALIAN DIAPHRAGM IN SURGICAL RECONSTRUCTION

CROSS-REFERENCE TO RELATED APPLICATION

The invention disclosed and claimed herein is generic to the invention described in United States patent application Ser. No. 925,108 which discloses the use of crosslinked anisotropic xenogeneic diaphragm tissue in flexor tendon pulley reconstruction.

FIELD OF THE INVENTION

This invention relates to xenogeneic tissue implantation in human tissue repair and prostheses.

BACKGROUND OF THE INVENTION

Implantation in humans of xenogeneic tissue, i.e. tissue from a species other than human, has been carried on extensively for more than two decades. Xenogeneic implants are useful in replacing human tissues which are damaged by pathological or traumatic injury. Such implants have been used for replacing heart valves, ligaments, tendons and skin, for example. Many techniques for preparation and treatment of xenogeneic tissue have been developed for many types of prosthetic and tissue repair applications in the human body. For example, treatment of such tissue with collagen in various forms and degrees of denaturization are known (U.S. Pats. No. 3,563,228, Seiderman, 3,949,073, Daniels et al, and 4,233,360, Luck, et al.) Treatment of graft tissues with aldehydes, and glutaraldehyde in particular, is well known (see, for example, U.S. Pat. No. 3,988,872, Dardik, et al., which is but one of many disclosures of the use of glutaraldehyde in tissue treatment).

Exemplary of the state of the art are the following U.S. Patents: Angell et al, U.S. Pat. Nos. 4,035,848 and 4,247,292 and Hancock, et al, U.S. Pat. No. 4,050,893—glutaraldehyde treatment of porcine heart valves; Schechter, U.S. Pat. No. 4,120,649—glutaraldehyde treatment of pigskin, human tissue, and amniotic membranes; Holman, et al, U.S. Pat. Nos. 4,239,492 and 4,240,794—glutaraldehyde treatment of umbilical cord tissue for vascular grafts; Ketharanathan, U.S. Pat. No. 4,319,363—glutaraldehyde treatment of artificially induced tubular structure of collagenous tissue; Lentz et al, U.S. Pat. No. 4,323,358—treatment of implant tissue with glutaraldehyde and wetting agent; Wright, U.S. Pat. No. 4,350,492, and Lane, U.S. Pat. Nos. 4,372,743 and 4,443,895—heart valve prosthesis from glutaraldehyde treated porcine heart valve; Kurland, U.S. Pat. No. 4,400,833—tendons and ligaments from cows and pericardium or other porcine tissue treated with glutaraldehyde and reinforced with synthetic mesh structure mesh structure; Pollock, et al, U.S. Pat. No. 4,402,697—treatment of implant tissue with phosphate ester and glutaraldehyde; and Pollock, U.S. Pat. No. 4,405,327 treatment of implant tissue with quaternary ammonium compounds and glutaraldehyde.

The temporomandibular joint, referred to also as the TMJ, is commonly known as the lower jaw. The articulation mechanism of the temporomandibular joint comprises a glenoid cavity and an intra-articular fibrocartilage with synovial membrane above and below it, and a bony condyle. The fibrocartilage helps the condyle to glide, revolve and rotate. The fibrocartilage accepts the repetitive compressive stresses resultant from eating, speaking and mouth motions.

In the patient with degenerative bone disease, the temporomandibular joint may become dysfunctional, resulting in pain as well as loss of function, i.e. the lower jaw may simply lock in a position or have limited motion. In such patients, the fibrocartilage as well as the condylar surface have been destroyed by the degenerative processes. Currently, the primary indication for temporomandibulr joint surgery is the alleviation of pain, with little hope for recovery of full function.

There are, of course, many prosthetic and repair materials available. Synthetic materials, such as Proplast⊥ or silicone, and xenogeneic tissue or allograft tissue, such as freeze-dried dura matter (a connective tissue membrane which covers the brain), or fascia lata (a connective fibrous tissue from beneath the skin) have been tried as temporomandibular joint condylar resurfacing materials.

As more fully discussed in the copending application of the present inventor and Dr. Royce C. Lewis, Jr., entitled CROSSLINKED ANISOTROPIC XENOGENEIC DIAPHRAGM TISSUE IN FLEXOR TENDON PULLEY RECONSTRUCTION, filed on the even date herewith, the fibro-osseous sheath of the hand flexor tendon is composed of thickened areas of arced fibers (annular pulleys), alternating with crisscrossed fibers (cruciate pulleys). The function of the pulleys is to enhance flexor tendon gliding function by holding the tendons close to the phalanges to prevent them from "bowstringing" during flexion and extension.

There are also prosthetic and repair materials available for reconstruction of the flexor tendon pulley. Synthetic materials, such as Teflon TM, dacron, Nitex TM, and xenogeneic tissue or allograft tissue such as bovine or porcine pericardia, fascia lata, and the like have been suggested as flexor tendon pulley repair materials; however, as pointed out by Dixon and Lewis, supra, synthetics tend to be unduly bulky or thick, and can cut into the tendon, and can also result in a high inflammatory response due to particulate abrasion. Uncrosslinked or insufficiently crosslinked xenogeneic tissue and allograft tissue may lose mechanical properties as a result of rapid tissue remodeling under the stress of use, with a return of the pre-operative problems and symptoms. Available crosslinked xenogeneic tissues, such as bovine or porcine pericardial tissue, do not possess the necessary properties for the reapir of structures characterized by high pressure and relative movement and thus stretch and allow adhesion formation.

There exists a continuing and long standing need for better structural replacements for anatomical structures which are in contact with other moving anatomical structures and which are under substantial force or pressure from the moving structure. Typical of these are synovial membranes and fibrocartilage structures such as those described above.

An improved xenogeneic tissue is disclosed as the present invention which solves or greatly mitigates the problems in certain indications which are prevalent in the prior art.

SUMMARY OF THE INVENTION

A xenogeneic tissue graft for replacement of synovial membrane or fibrocartilage tissue comprising crosslinked anisotropic mammalian diaphragm having a smooth serous side and a fibrous side is described. The anisotropic, crosslinked mammalian diaphragm graft of this invention is characterized in that the graft has one smooth side adapted to be positioned against a moving structure in the human body to permit non-adhesive or low-adhesive movement of the same, and a rougher fibrous side opposig side adapted to permit ingrowth of tissue. In a preferred form, the anisotropic, crosslinked diaphragm graft is of bovine or porcine origin.

In a particular exemplary embodiment the xenogeneic tissue replacement graft of this invention is specifically prepared and configured for the replacement of nonfunctional fibrocartilage of degenerated human temporomandibular.

The invention also contemplates an exemplary method of tissue replacement for nonfunctional fibrocartilage of a degenerated human temporomandibular joint comprising debridement of the nonfunctional fibrocartiliage and replacing the same with crosslinked anisotropic mammalian diaphragm.

A method for repairing a degenerate temporomandibular joint in which crosslinked bovine, porcine or other anisotropic mammalian diaphragm is formed and cut and used surgically to replace nonfunctional fibrocartilage of the temporomandibular joint, and such xenogeneic tissue are disclosed as a preferred example of the application of this invention.

The examples of application of the principles of this invention given above are not limiting. The graft material and method of this invention may be used to advantage whereever one part of the body is constructed to move in non-adhesive or low-adhesive relationship to another part of the body, and is particularly applicable to such areas where forces and pressures are high, such as, for example, in or adjacent joints where there is substantial relative movement between bone and tissue, tendon and tissue, tendon and bone, etc.

DESCRIPTION OF THE PREFERRED EMBODIMENT

Bovine or porcine or other anisotropic mammalian diaphragm is obtained, stripped of fat and other nonessential tissue and cleaned according to standard techniques used in obtaining xenogeneic tissue. The diaphragm is crosslinked using known methods. The diaphragm is characterized by having one smooth serous side, and one rough, fibrous side, the importance of which structure will be apparent as the method of use is described.

As illustrated by the previously cited prior art, glutaraldehyde has been reported as being effective in reducing antigenicity and reducing the likelihood of infection. Glutaraldehyde crosslinks proteins rapidly and effectively, and causes the cross-linking of proteins in the tissue being treated. This treatment increases resistance to proteolytic cleavage and hence increases resistance to enzymatic degradation. The treatment of implant tissue with glutaraldehyde is sometimes referred to as "tanning" because it cross-links links the protein and inhibits enzymatic and biochemical degradation of the tissue, comparable in general to the effect of tanning leather. Glutaraldehyde is also often used as the preservative in aqueous solution for storing tissues after treatment.

Crosslinking of the protein in the tissue may be accomplished in a number of ways and any crosslinking reagent may be used. Glutaraldehyde is one of the preferred reagents. Other aldehydes, however, or other crosslinking materials may be used. The crosslinking can be carried out in any desired method. Many such methods are described in the prior art. Generally, the crosslinking step comprises soaking the tissue in glutaraldehyde solution, or other aldehyde containing solution, for from a few minutes to several days, depending upon the rate of crosslinking reaction. The rate of crosslinking reaction can be controlled by controlling the concentration of glutaraldehyde and, to a lesser extent, by controlling the pH and/or the temperature of the crosslinking reagent. The concentration of the glutaraldehyde is typically from about 0.1% to 5.0%. The solution is typically buffered to about pH 7 to 9 with any suitable buffer., e.g. conventional bicarbonate, citrate, and phosphate buffers and the like. Time and concentration are, of course, related and considerable variation in both are well known in the art. The solution may include one or a number of crosslinking materials, such as, for example, formaldehyde, glyoxal,and/or dialdehyde starch. This step is, of course, well known and reference may be made to any number of prior art patents and publications for guidance as to this step. For example, one well known treatment method for crosslinking tissue, i.e. crosslinking the proteins in the tissue, is described by Yarbrough, et. al; Structural alterations in tissue cardiac valves implanted in patients and in calves., *J Thoracic and Cardiovascular Surgery*, March 1973, pp. 364–74.

Generally cleaned bovine or porcine or other anisotropic mammalian diaphragm tissue, prepared by removal of fat and foreign tissue and trimmed in the usual manner to form membrane layers, each having a smooth serous side and a rough fibrous side. The membrane is then soaked, either free-floating or in a fixed configuration as desired, in glutaraldehyde solution, as described hereinbefore, and in the prior art, such as, for example, in Yarbrough et al, supra. The crosslinked mammalian diaphragm is sterilized, if necessary, and is washed thoroughly to remove all traces of unreacted glutaraldehyde and other chemicals used in preparation.

The crosslinked anisotropic graft is then cut to the appropriate size, which is determined in each case by the size of the articulation joint of the temporomandibular joint of the particular patient. After debridement of the nonfunctional host graft, the fibrous side of the crosslinked cow diaphragm is laid down on the prepared bony bed with the smooth side up towards the synovial membrane. The diaphragm graft is carefully sutured down using standard fixation techniques, and the surgery is completed in accordance with usual surgical procedures.

By way of illustration, and not or limitation, a simple example of the present invention is given, with the caution that adaptations and adjustments may be made without departing from the invention. Fresh bovine or porcine diaphragm tissue is received from the slaughter house, inspected to meet vendor specifications, and thoroughly rinsed in pH 7.4 phosphate buffered solution. The diaphragm tissue is dissected, separating and discarding all fat tissue and extraneous connective tissue and blood vessels, to leave only a smooth serous side and a fibrous side. The fibrous side is thinned down to a maximum of 0.5 mm using pathology scalpels. The dissected tissue is cut into smaller pieces of usable areas. This tissue is submerged in a suitable container of 0.2% phosphate buffered glutaraldehyde pH 7.4 and kept at room temperature. The submerged tissue is laid flat in the container and left unstressed. The container is kept closed to eliminate the possibility of contamination to the tissues, and Good Laboratory Practice Regulations and Good Manufacturing Practice Regulations are followed at all phases of the process. After 24 hours has elapsed, the tissue is turned and the solution discarded and fresh 0.2% buffered glutaraldehyde is added until the tissue is completely submerged. This procedure is repeated at 48 and 72 hours. After 96 hours, samples of the crosslinked tissue are tested using standard Shrinkage Temperature testing apparatus and procedures to assure adequate crosslinking. The crosslinked tissue is aseptically dissected to final configuration under sterile environment, such as, for example, a Class 100 Laminar Flow Bench. The final configuration of the TMJ replacement material should normally be about 20 mm wide, 40 mm long, and about 0.5 mm thick, though the exact dimensions will depend upon the particular patient and procedure for which the tissue is being prepared. Dimensioning is accomplished using a fine scalpel for dissection to meet particular size requirements. In preparing tissues for sale or distribution, a series of tissues ranging from about 12 mm×30 mm to about 30 mm×50 mm in width and length are prepared thus permitting the surgeon to select the appropriate size. The surgeon can, of course, modify a given size to meet a particular requirement as determined during surgery. The tissue is inspected by Quality Assurance to assure compliance with all specifications, packaged in an approved container of sterile physiologic saline and radiation sterilized.

The crosslinked anisotropic mammalian diaphragm is biocompatible, allows good dense connective tissue to overgrow and ingrow the graft to regain condylar height and function, and has sufficient mechanical strength and compressibility to perform entirely satisfactorily, and is easy to suture in place during surgery.

INDUSTRIAL APPLICATION

The tissues of the invention are suitable for shipment and sale as human implants.

What is claimed is:

1. A xenogeneic tissue graft for replacement of synovial membrane or fibrocartilage tissue comprising crosslinked anisotropic mammalian diaphrapm having a smooth serous side and a fibrous side.

2. An anisotropic, crosslinked mammalian diaphragm graft characterized in that the grat has one relatively smooth side adapted to be positioned against a moving structure in the human body to permit non-adhesive movement of the same, and one relatively rougher fibrous side adapted to permit ingrowth of tissue.

3. An anisotropic, crosslinked bovine or porcine diaphragm graft characterized in that the graft has one smoother side adapted to be positioned against a moving structure in the human body to permit non-adhesive movement of the same, and a rougher fibrous side adapted to permit ingrowth of tissue.

4. A method of reconstructing the human temporomandibular joint comprising replacing temporomandibular fibrocartilage with xenogeneic tissue graft comprising crosslinked anisotropic mammalian diaphragm having a smooth serous side and a fibrous side, the fibrous side being sutured against the body leaving the smooth side to receive the condyle of mandible permitting relative movement thereof.

* * * * *